United States Patent [19]

Smidt

[11] Patent Number: 4,824,103

[45] Date of Patent: Apr. 25, 1989

[54] MUSCLE TESTING AND EXERCISING APPARATUS

[76] Inventor: Gary L. Smidt, 8 W. Park Rd., Iowa City, Iowa 52240

[21] Appl. No.: 168,002

[22] Filed: Mar. 14, 1988

[51] Int. Cl.⁴ .......................... A63B 21/00; A61B 5/22
[52] U.S. Cl. .................................... 272/125; 128/782;
   272/DIG. 5; 73/379; 73/381
[58] Field of Search ......... 272/125, 126, 129, DIG. 4,
   272/DIG. 5, DIG. 6; 73/379, 380, 381;
   128/774, 777, 779, 781, 782

[56] References Cited

U.S. PATENT DOCUMENTS

| | | | |
|---|---|---|---|
| 3,680,386 | 8/1972 | Cannon | 73/381 X |
| 4,180,059 | 12/1979 | Tiep | 128/782 |
| 4,436,099 | 3/1984 | Raftopoulos | 128/782 |
| 4,501,148 | 2/1985 | Nicholas et al. | 73/379 |
| 4,553,746 | 11/1985 | Lee | 272/DIG. 5 X |

FOREIGN PATENT DOCUMENTS 3038724  5/1982  Fed. Rep. of Germany ...... 272/125

Primary Examiner—Richard J. Apley
Assistant Examiner—Joe H. Cheng
Attorney, Agent, or Firm—Epstein & Edell

[57] ABSTRACT

Different attachments that are connectable to a force transducer in easily interchangeable manner via standardized quick-disconnect coupling arrangements facilitate multiple use and applicability to testing and exercising of a great variety of muscle groups of the human body in compression and tension modes. Microprocessor supervision and control of testing and exercising procedures, providing various direct measurement outputs and testing, exercising, and training criteria as well as characteristic time-dependent measures, allow applicability to a plurality of muscle testing and exercising tasks in clinical, therapeutic, recreational and sport-training situations. Ease of adaptability of the force transducer unit together with the microprocessor control to different tasks facilitates use and operation as well as interpretation of results by persons without the specialized skills heretofore required. Compactness and light weight of the arrangement assures portability.

20 Claims, 12 Drawing Sheets

MUSCLE TESTING AND EXERCISING APPARATUS

BACKGROUND OF THE INVENTION

1. Technical Field

This invention relates to muscle dynamometers and more muscle exercising instruments, and, more particularly, to an improved multiple-use apparatus for testing and exercising most human muscle groups.

2. Discussion of the Prior Art

Exercising devices and, similarly, muscle strength testing devices are well known in the prior art. For instance, exercising devices are shown in U.S. Pat. Nos. 1,023,756 (Pons); 4,376,533 (Kolbel); 3,759,514 (Cox); and 4,211,405 (Blowsky et al). These patents disclose various exercising devices utilizing push and pull (compression and tension) operating modes with use limited to exercising upper and/or lower extremities. The patent to Pons shows displacement graduations to provide force or strength indication during exercising. U.S. Pat. No. 3,784,195 (Johnson) discloses a push pull exerciser device having one end attached to a fixed surface and having its other end equipped with a two-hand handle without any provision for measurement of force. U.S. Pat. No. 3,902,480 (Wilson) discloses an electro-mechanical system that relates substantially only to provision of isotonic or isokinetic motion for exercise training.

U.S. Pat. No. 4,408,183 (Wills) discloses an exercise monitoring device for measuring force, for variously timing force application, and for counting the number of repetitions of particular exercises. U.S. Pat. Nos. 4,170,225 (Criglar et al); 4,246,906 (Winberg et al); 4,450,843 (Barney et al); and 4,461,301 (Ochs) show a variety of biofeedback devices, not necessarily intended specifically for use in muscle exercising or testing. Biofeedback systems employable in conjunction with muscle training and testing are disclosed in U.S. Pat. Nos. 3,916,876 (Freeman) and 4,110,918 (James et al). U.S. Pat. No. 4,571,682 (Silverman et al) discloses a system for acquisition, various processing, and display of a variety of physiological measures for use in enhancement of skilled performance or behavior.

As indicated above, the prior art shows a number and variety of small and lightweight relatively specialized testing and exercising devices, each having a particular use in either testing or exercising and being applicable to comparatively few groups of muscles. Some devices provide only tension and some only compression facilities while some provide both; others provide for force measurement, yet others offer only qualitative dynamometric indication, etc. More universally-applicable, lightweight and compact multiple-use devices for testing and exercising of most muscle groups of the human body of interest in training and in evaluation of muscle performance and training progress as well as in medical clinical tasks, adaptable both in their interfacing facilities and in their measurement acquisition, handling, processing, and display and other output capabilities in adequately simple manner to permit use without specialized skill, have neither existed nor been suggested heretofore.

OBJECTS AND SUMMARY OF THE INVENTION

It is therefore an object of the present invention to provide an apparatus for testing and exercising of muscles, which device is easily adaptable for multiple uses and thus universally applicable to a great variety of muscle groups of the human body in a variety of operating modes. It is a further object of the present invention to provide that apparatus such that it adapts easily for operation in compression or tension, is portable and hand-held, and is controlled by a microprocessor which further supervises, in conjunction with memory: an input keyboard; interfaces and other auxiliary hardware;; and various system functions; and which provides for appropriate output for indications, displays, printers, recorders, etc.

More particularly, it is an object of the present invention to provide a force sensor device for use in muscle exercising and testing, including various attachments for interfacing compressionally or tensionally with, and being suitable for, fastening to, holding by, or contacting: human extremities, head and torso or trunk various muscle groups; or rigid or movable extracorporeal objects.

It is a further object of the present invention to provide an apparatus for use in muscle exercising and testing for acquisition, handling and processing, and display as well as other output capabilities of muscle force and other physiological measurement information obtained in testing and/or exercising of muscles from an appropriate multiple-use sensor in order to provide information on muscle strength and exercise performance and varous derived measures of performance (e.g., muscle development, endurance and other time-dependent measures), as well as providing force threshold and exercise target criteria in order to facilitate muscle exercising and testing.

It is still another object of the present invention to provide a multiple-use muscle exercising and testing apparatus that is lightweight and compact in size so as to be portable, as opposed to conventionally known exercising and testing machines that often exceed the ability of a single person to carry and move the device.

It is yet another object of the present invention to provide a multi-purpose muscle exercising and testing apparatus that facilitates use and operation as well as interpretation of results by persons without the specialized skills heretofore required for such tasks.

In accordance with the present invention, a force transducer or load cell is provided within an appropriate compact and lightweight housing having two opposed universal couplings for connection of different interchangeable attachments equipped with standardized mating couplers. Such attachments are used in pairs matched to particular functions to be performed. For instance, attachments may be suited for holding by a person, for contact with a person's body, or for fastening to a body part. They may be suited for attachment to inanimate objects such as walls, tables or weights. Different combinations of such attachments provide appropriate attachment pairs for different testing and-/or exercising purposes in tension or in compression. The transducer provides signals dependent upon the resulting force acting between the two attachments of a pair. A displacement transducer may be incorporated to provide additional signals directly dependent upon displacement between the two attachments of a pair.

The described transducer, which may be equipped with preamplifier circuitry within its housing, is connected via an appropriate electrical cable to a processor and control unit. The latter comprises a digital micropocessor including: a read-only memory for storing programs, data tables, and varous fixed information as may be needed; memory for processing; and further memory for temporary and long term storage of information. Further, the processor and control unit includes: analog-to-digital conversion circuitry to convert received transducer signals to a suitable form for further processing; timer clock and counter circuitry; keyboard, display, and communication interface circuitry; as well as a power supply for the various components. Additionally, output components, such as, for example, visual display and indicators, audible indicators, etc., are part of the processor and control unit.

The muscle testing and exercising apparatus of the present invention is operated by connecting an appropriate pair of attachments to the transducer unit, preselecting the appropriate processor and control unit input (and output), and activating the transducer unit being applied to testing or exercising a particular group of muscles. For example, when used in a simple mode representative of the general utilization to facilitate a basic understanding of the invention a pair of identical handle attachments is connected to the transducer unit for use in tension to test or exercise horizontal abductor muscles of the shoulder. Each handle is held in one hand and the subject exerts a force directed toward pulling the handles apart. The appropriately programmed processor and control unit produce and display output data representative of the force exerted at any particular time. Such output may also be indicated in the form of audible signals; likewise, preselected force threshold levels may be dispolayed, instances of attaining or exceeding of such thresholds may be indicated and counted, timing of the exercise/test may be effected, etc. Characteristic values (e.g., representing measures of endurance, peak strength, variability of force, and rate of force development) may all be displayed as well as stored for further processing (for example, for purposes of recording or printing performance and for use during subsequent future operation). It will be further appreciated that such testing use applies equally well to exercising, although different output parameters may be preselected to the extent that they may be of significance to the user.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference numerals refer to like parts throughout different views. The drawings are schematic and not necessarily to scale, emphasis instead being placed upon illustrating principles of the invention.

DESCRIPTION OF THE PREFERRED EMBODIMENTS

Figure 1:
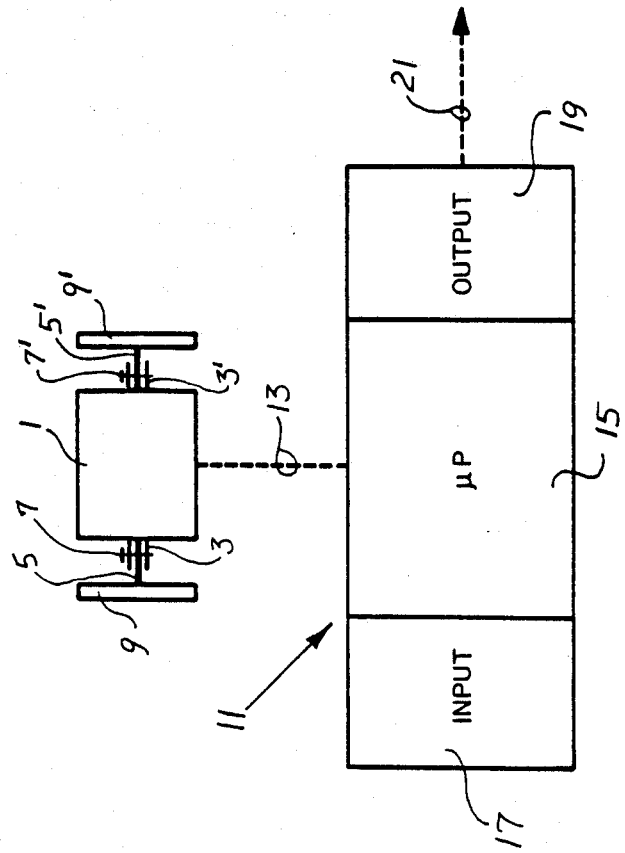
FIG. 1 is a schematic block diagram of the main components of a preferred embodiment of the present invention.

The block diagram as shown in FIG. 1 is representative of the overall system configuration of the present invention and indicates schematically the main components and their interrelationship. Transducer unit 1 is shown equipped with a pair of opposed and axially aligned female couplers, namely, left female coupler 3 on the left side and right female coupler 3' on the right side. Both couplers are substantially identical with exception of their manner and location of mounting to transducer unit 1. These couplers serve for coupling of various attachments, here schematically indicated as left attachment 9 on the left side and right attachment 9' on the right side, to transducer unit 1. For this purpose, attachments 9 and 9' comprise substantially identical male adaption couplers, namely left male coupler 5 and right male coupler 5', which mate with the respective female couplers 3 and 3'. Identical appropriately spring-loaded captive pins 7 and 7' serve as a quick-release locking arrangement for the locking together of mated male and female couplers and thusly for strong and secure retention of various attachments (indicated here by 9 and 9') on transducer unit 1.

Transducer unit 1 is interconnected via an electrical umbilical cable 13 with control processor unit 11 which basically comprises a microprocessor portion 15, input portion 17, output portion 19, and communication connections 21 for communication with external facilities.

Figure 3:
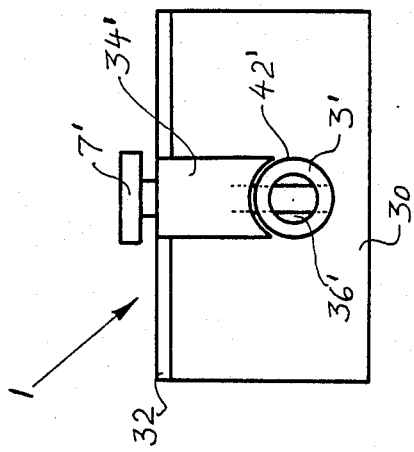
FIG. 3 is an end view of the transducer unit shown in FIG. 2.
Figure 2:
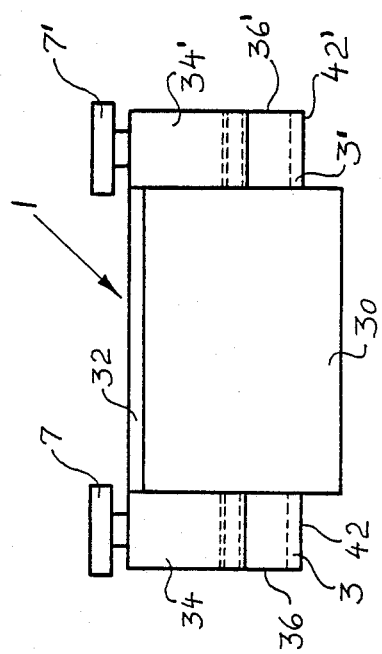
FIG. 2 is a side view of the transducer unit employed in the embodiment of FIG. 1, showing the arrangement of the female attachment couplers.

The side view of transducer unit 1 shown in FIG. 2 should be viewed in conjunction with the corresponding end view of the transducer unit illustrated in FIG. 3. Transducer unit 1 comprises a housing 30 having a cover 32. Housing 30 encloses and holds various appropriate transducer components such as a force transducer or load cell, preamplifier circuitry, calibration arrangements, cable connections, as well as fastening arrangements for mechanical coupling of the force to be sensed to the appropriate sensor part. As one portion of the force sensor itself is rigidly attached to transducer housing 30, it will be appreciated that one of the force transmitting couplers 3 or 3' is connected to the unattached active portion of the sensor and feeds through housng 30 without being substantially restrained from movement in the direction of the force strain relative to the housing; whereas the other coupler is fastened rigidly to transducer housing 30. For instance, left female coupler 3 is rigidly fastened to housing 30, for example with appropriate screw threads, and right female coupler 3' is attached to the active portion of the internal force sensor itself, for example also with screw threads, and feeds in unrestrained manner through housing 30.

Figures 4, 5:
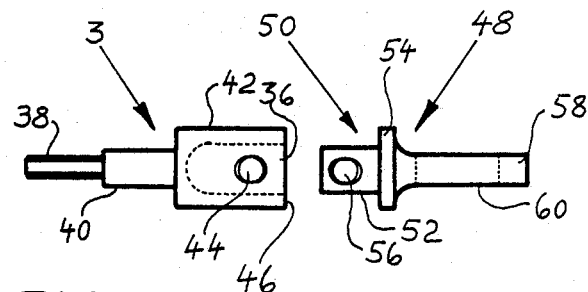
FIG. 4 is a top view of the female attachment coupler indicated in the arrangement shown in FIGS. 2 and 3.
FIG. 5 is a top view of a male attachment coupler as part of an eyelet attachment.
Figures 6, 7:
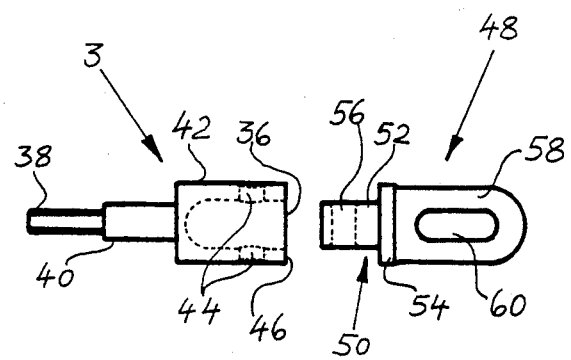
FIG. 6 is a side view of the female attachment coupler shown in FIG. 4.
FIG. 7 is a side view of the male attachment coupler shown in FIG. 5.

FIGS. 4 and 6 show female coupler 3 (or 3') in more detail. Coupler 3 (or 3') is of substantially multi-diameter stepped cylindrical shape having at one end a male threaded stud portion 38 continuing in a plain cylindrical stud portion 40 and ending in a larger diameter cylindrical head 42 that is provided with a blind coaxial coupler bore 36 to a depth somewhat less than the length of head 42. Head 42 is further provided with a diametral cross-hole 44 spaced some small distance from end face 46.

Returning to FIGS. 2 and 3, the manner in which transducer unit 1 is equipped with female couplers 3 an 3' can now be more easily visualized in view of the above description of the female coupler 3 and 3' in conjunction with FIGS. 4 and 6. For instance, female coupler 3 is rigidly fastened to transducer housing 30. Female coupler 3' is appropriately attached to the active portion of the internal force sensor itself by threaded engagement of threaded stud portion 38, whereby the plain cylindrical stud portion 40 feeds through an appropriate hole in transducer housing 30 having a small diametral clearance to allow axial coupler displacement, but substantially no radial or angular movement. Both couplers are arranged in coaxial alignment and are substantially identical, at least with respect to the structure and size of cylindrical head 42 which is an essential component of the standardized mating coupling arrangements for a plurality of different attachments to transducer unit 1.

FIGS. 5 and 7 show an example of a particular attachment, namely eyelet attachment 48, incorporating the male coupler 50 (also schematically indicated in FIG. 1 as male coupler 5 or 5') which is another essential component of the standardized coupling arrangement. In the engagement of transducer unit 1 with an attachment, such as, for instance, eyelet attachment 48, male coupler 50 fits with its cylindrical boss 52 into coupler bore 36 within female coupler 3. Stop collar 54 of male coupler 50 limits the insertion depth of boss 50 into bore 36. Boss 52 is provided with a diametral engagement hole 56 that is of substantially the same diameter as cross-hole 44 in cylindrical head 42 of female coupler 3. In the mating engagement of female and male couplers, pin 7 (indicated in FIGS. 1 through 3) fits through coaxially aligned holes 44 and 56 to suitably fasten an attachment, for example eyelet attachment 48, to transducer unit 1.

Referring to FIGS. 2 and 3, identical appropriately spring-loaded captive pins 7 and 7' are held within identical pin casings 34 and 34', respectively. Pin casing 34 incorporates suitable structures for spring-loading pin 7 in the downward direction to assure pin engagement across the full diameter of the cylindrical head 42, as indicated in FIG. 3. Pin casing 34 also incorporates suitable structure to allow partial upward withdrawal of pin 7 from the casing (against the spring-loading), such that pin 7 disengages entirely from head 42, and structure for pin 7 to be captively retained within casing 34. Pin 7 is not only axially movable within casing 34, but it is arranged to have radial clearance, at least in the direction of applicable transducer sensor strain, in such a manner as to permit easy and largely frictionless radial displacement by an amount substantially equal to or slightly in excess of the maximum allowable transducer sensor strain commensurate with the rated force range. In this manner, pin 7 is appropriately advantageously retained by the arrangements of its casing 34 on transducer housing 30, yet it is substantially free to move with the axial displacement motion of mated couplers 3 (respectively 3') and 50 as a consequence of axial forces applied during operation.

The example of an eyelet attachment 48 shown in FIGS. 5 and 7 comprises, in addition to the male coupler 50, the eyelet per se which may be essentially a continuous eyelet loop 58 of appropriate high-strength material that is an extension on the end of male coupler 50 beyond collar 54 and that surrounds eyelet opening 60. It should be appreciated that eyelet loop 58 of eyelet attachment 48 may be shaped in various appropriate ways to suit different uses. For instance, eyelet loop 58 may be circular surrounding a circular hole or it may be a hook-shaped open loop.

Figure 8:
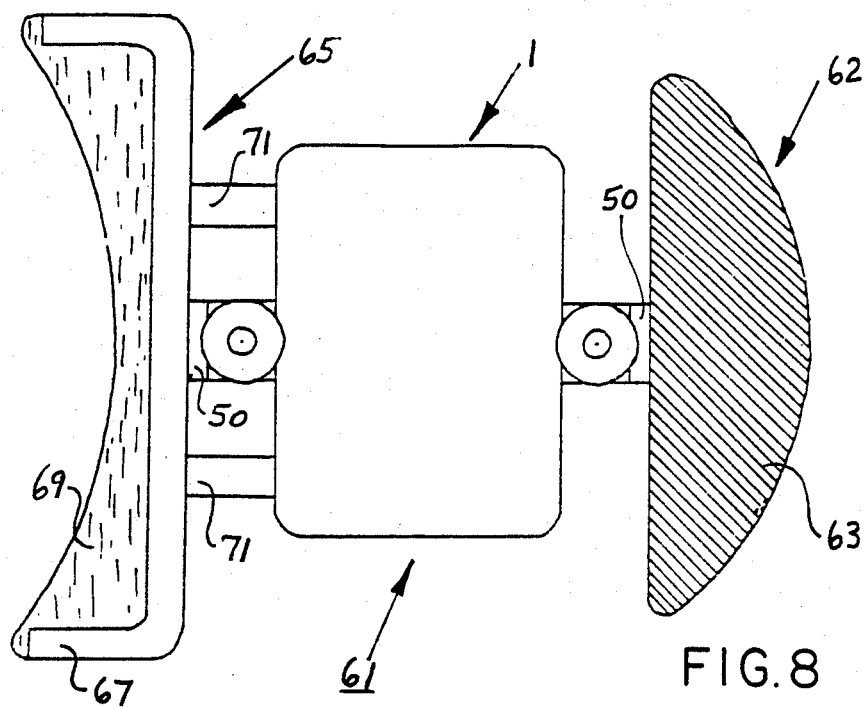
FIG. 8 is a plan view of the transducer unit equipped with a mushroom handle attachment and a force application pad attachment.
Figure 9:
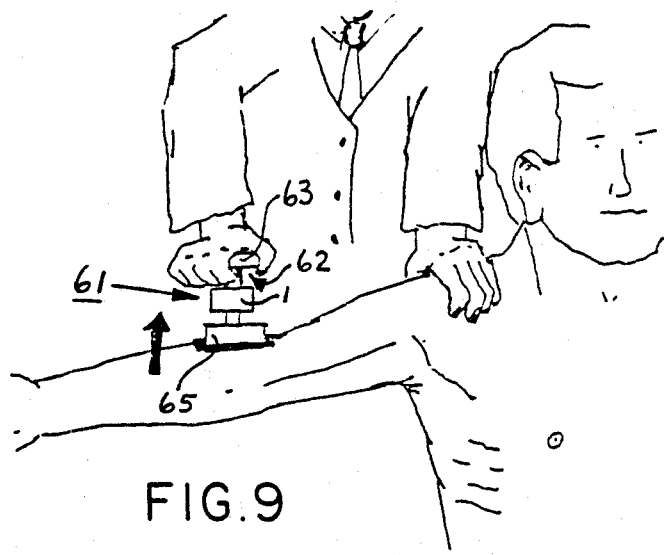
FIG. 9 shows a pictorial illustration of an example of the arrangement of FIG. 8 in a particular use situation.

FIG. 8 schematically depicts a compression force application arrangements 61 of transducer unit 1 to which a mushroom handle attachment 62 is coupled on the right side (i.e., in this case, the side that couples to the active portion of the internal force sensor). Mushroom handle attachment 62 comprises mushroom head 63 attached to male coupler 50 which mates with female coupler 3 (not specifically shown here, but previously shown and described). A force application pad attachment 65 is coupled to the left side of transducer unit 1. Attachment 65 comprises a pad base 67 equipped with resilient padding 69, male coupler 50, and at least two supports 71 which seat on transducer unit 1 for more rigid support when the pad attachment 65 is coupled to transducer unit 1 in the manner previously described. It will be appreciated that this pad attachment 65 is coupled to the transducer unit housing 30 as also previously described. The force application arrangement 61 is shown in an example of use in FIG. 9 for measurement of strength of the shoulder abductor muscles. As depicted, mushroom head 63 is grasped with the hand of the examiner, and force application pad attachment 65 is forced against a particular body part of the subject. The subject's reaction force is sensed by transducer unit 1 and the desired measure of strength is thusly obtained. It should be understood that the force application pad attachment may vary to accommodate various body segments; for example small sizes for the fingers and large sizes for use on the torso or trunk.

Figure 10:
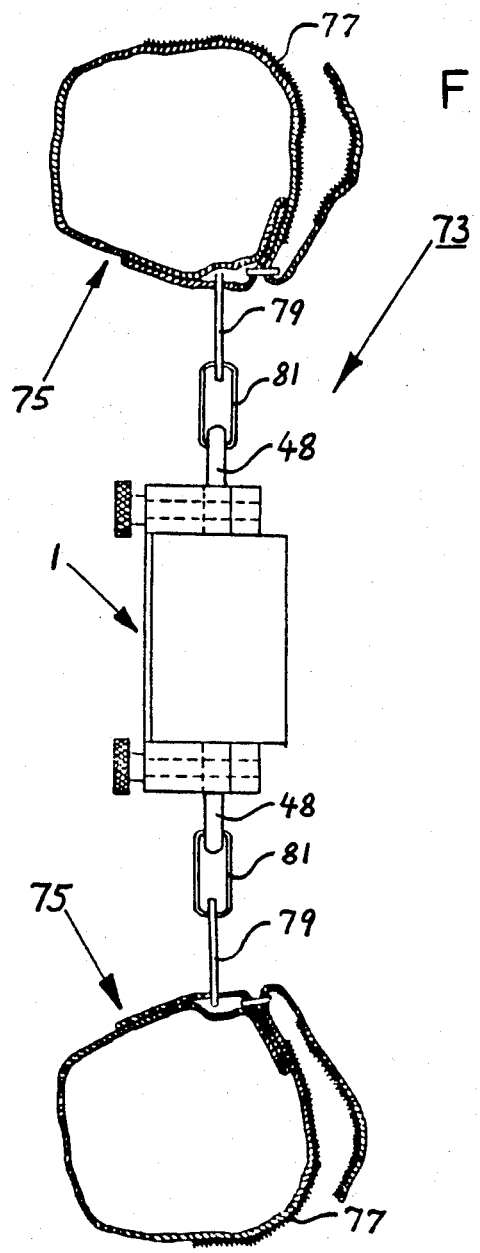
FIG. 10 is a side view of the transducer unit equipped with body cuff attachments.
Figure 11:
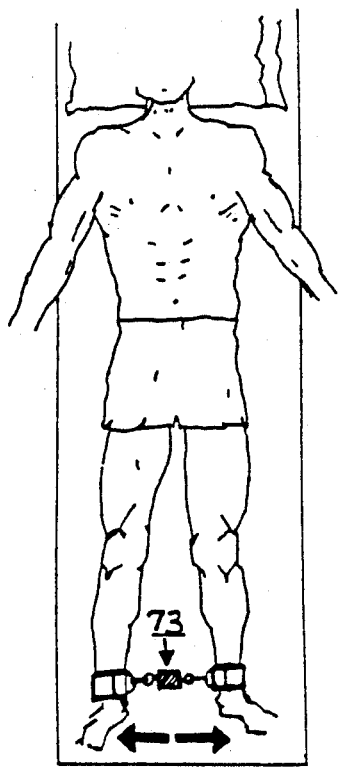
FIG. 11 shows a pictorial illustration of an example of the arrangement of FIG. 10 in a particular use situation.

FIG. 10 schematically depicts a tension arrangement 73 for which transducer unit 1 is equipped with a pair of identical body cuff attachments 75 appropriately coupled to transducer unit 1 with standardized couplers as previously described. Each attachment 75 comprises an adjustably tightenable cuff 77 engaged to a connector 79 connected to link 81 that in turn engages an eyelet attachment 48 (incorporating previously described standardized male coupler 50) coupled to transducer unit 1. Tension arrangement 73 is shown in an example of use in FIG. 11 for muscle strength measurement and exercise purposes when cuffs 77 are fastened about a user's ankles.

Figure 12:
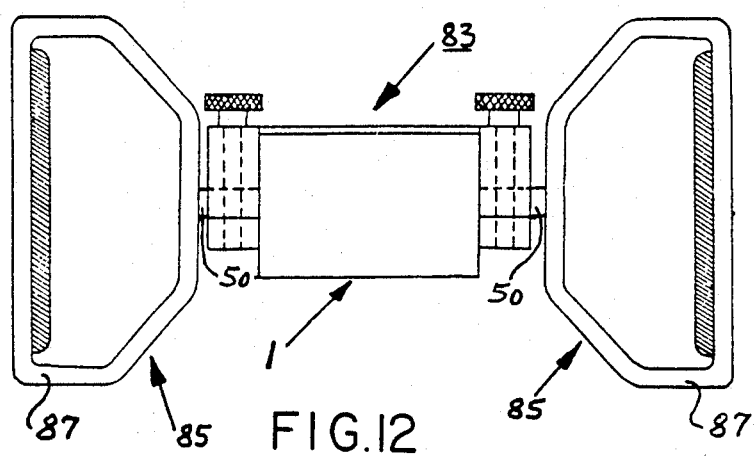
FIG. 12 is a side view of the transducer unit equipped with a pair of single handle attachments.
Figure 13:
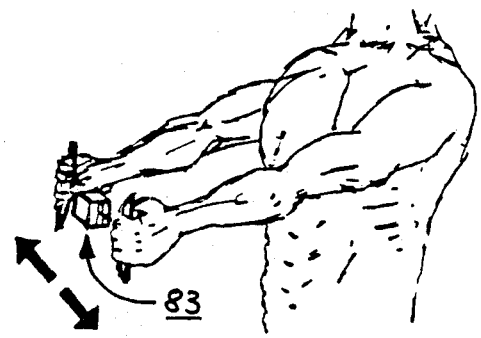
FIG. 13 shows a pictorial illustration of an example of the arrangement of FIG. 12 in a particular use situation.

FIG. 12 shows a push-pull handle arrangement 83 for which transducer unit 1 is equipped with a pair of identical handle attachments 85. Each handle attachment comprises handle 87 fastened to male coupler 50 which is coupled to transducer unit 1 in the manner previously described. Handle arrangement 83 is illustrated in an example of use in FIG. 13 wherein it is shown appropriately held in both hands for purposes of testing and exercising muscle groups in the arms and upper body both in tension and in compression.

Figure 14:
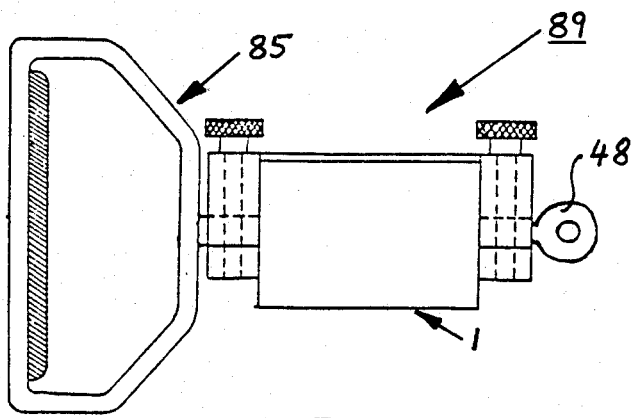
FIG. 14 is a side view of the transducer unit equipped with a single handle attachment and an eyelet attachment.
Figure 15:
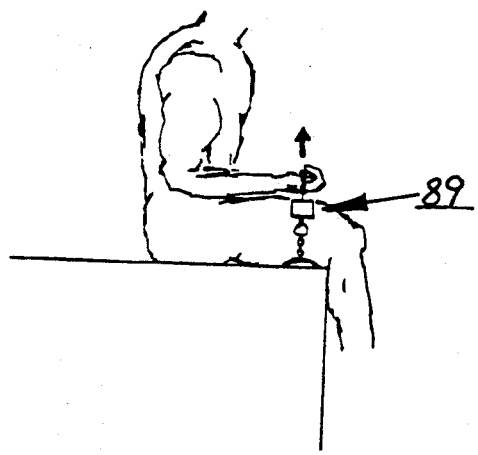
FIG. 15 shows a pictorial illustration of an example of the arrangement of FIG. 14 in a particular use situation.

FIG. 14 depicts a single handle combination arrangement 89 for which transducer unit 1 is equipped with handle attachment 85 on one side and eyelet attachment 48 on the other side. This handle arrangement 89 is illustrated in an example of use in FIG. 15 wherein eyelet attachment 48 is appropriately fastened to a rigid object, for instance a table, and handle attachment 85 is grasped in one hand. Testing and exercising in tension is thusly facilitated, for example as shown in FIG. 15 with respect to elbow flexor muscles.

Figure 16:
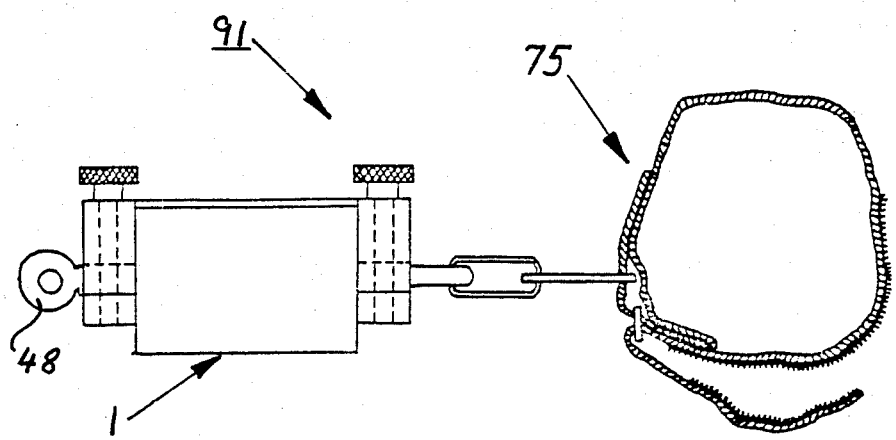
FIG. 16 is a side view of the transducer unit equipped with a body cuff attachment and an eyelet attachment.
Figure 17:
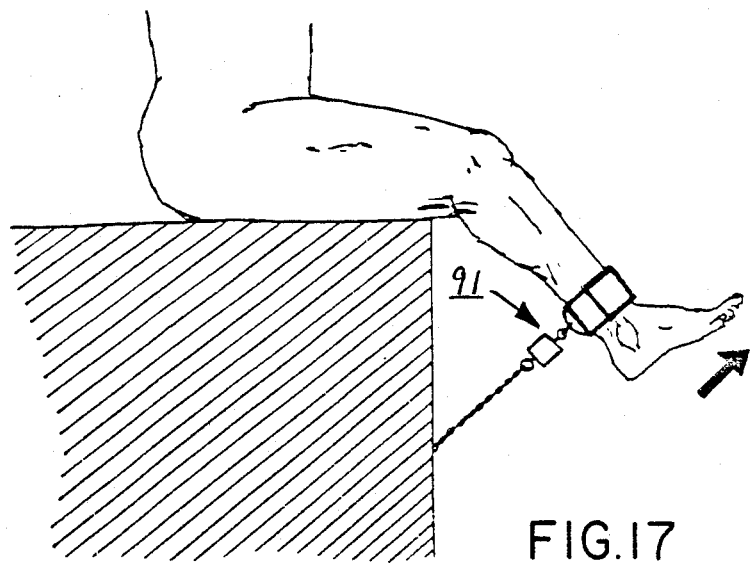
FIG. 17 shows a pictorial illustration of an example of the arrangement of FIG. 16 in a particular use situation.

FIG. 16 shows a cuff combination arrangement 91 for which transducer unit 1 is equipped with body cuff attachment 75 on one side and eyelet attachment 48 on the other side. Cuff arrangement 91 is illustrated in an example of use in FIG. 17 wherein eyelet attachment 48 is appropriately fastened to a rigid object, for instance a table, and cuff attachment 75 is fastened to the lower leg. Testing and exercising in tension is thusly facilitated, for example as shown in FIG. 17 in respect to the knee extensor muscles.

Figure 19:
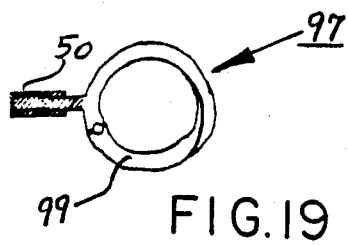
FIG. 19 is a side view of a clasp attachment for the transducer unit.

FIG. 19 depicts a clasp attachment 97 that is substantially similar to eyelet attachment 48 in most respects, except that a hinged portion 99 of its eyelet permits its opening to facilitate engagement of various other components. Clasp attachment 97 also incorporates standardized male coupler 50 for coupling to transducer unit 1.

Figure 18:
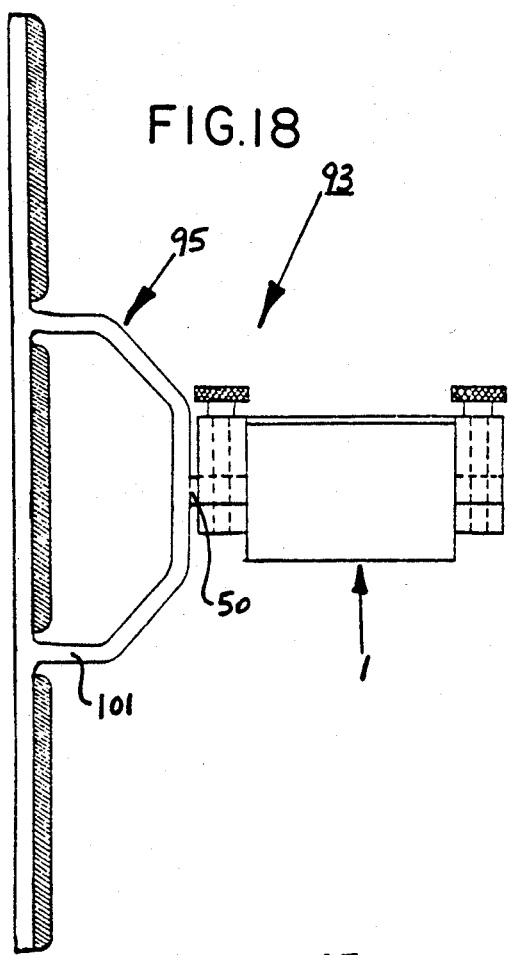
FIG. 18 is a side view of the transducer unit equipped with a multiple handle attachment on one side.
Figure 20:
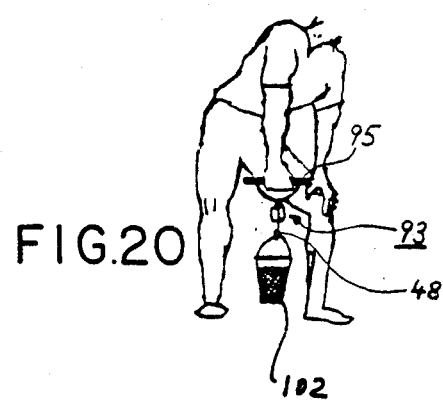
FIG. 20 shows a pictorial illustration of an example of an arrangement of the transducer unit equipped on one side with the multiple handle attachment as shown in FIG. 18, and, on the other side, equipped either with the clasp attachment, as shown in FIG. 19, or alternately with the eyelet attachment of FIGS. 5 and 6, in a particular use situation.
Figure 21:
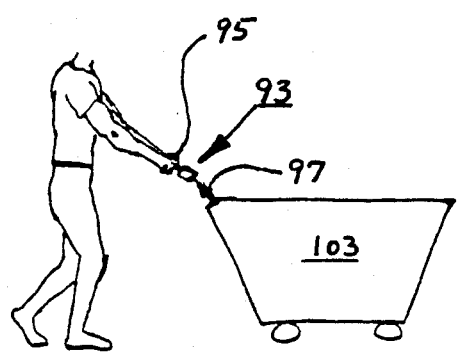
FIG. 21 shows a pictorial illustration of the attachment-equipped transducer unit arrangement depicted in FIG. 20 in another particular use situation.

FIG. 18 shows a multiple handle combination arrangement 93 for which transducer unit 1 is equipped with multiple handle attachment 95 on one side and, for example, an eyelet attachment 48 (such as shown in FIG. 7) or a clasp attachment 97 (such as shown in FIG. 19) coupled to transducer unit 1 on the other side. Multiple handle attachment 95 comprises multiple handle 101 and standardized male coupler 50. Arrangement 93 in combination with mated eyelet attachment 48 is illustrated in an example of use in FIG. 20 wherein eyelet attachment 48 is appropriately fastened to a weight 102 and multiple handle attachment 95 is grasped in one hand. Testing and exercising in tension is thusly facilitated for instance in the lifting exercise shown. Arrangements 93 in combination with mated clasp attachment 97 (of FIG. 19) is illustrated in an example of use in FIG. 21 wherein clasp attachment 97 is appropriately fastened to the handle of cart 103 and multiple handle attachment 95 is grasped by both hands. Testing and exercising in tension and compression is thusly facilitated, for example for ergonomic purposes in the workplace.

Figure 22:
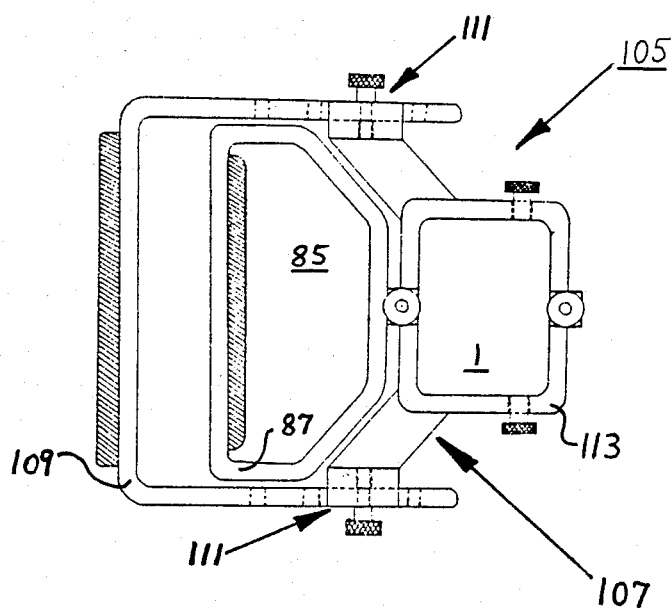
FIG. 22 is a top view of the transducer unit equipped with a pair of two dissimilar handle-like attachments.
Figure 23:
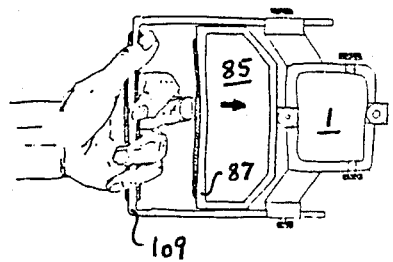
FIGS. 23 and 24 show pictorial illustrations of two examples of the transducer unit arrangement of FIG. 22 in two different use situations.
Figure 24:
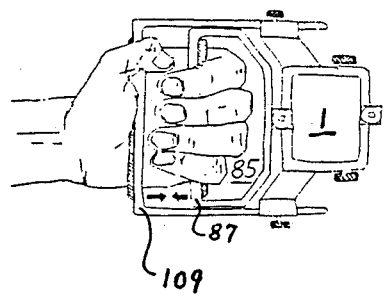

FIG. 22 depicts a finger handle arrangement 105 for which transducer unit 1 is equipped with handle attachment 85 (that is coupled to the active transducer sensor side within transducer unit 1) and with a special grip frame attachment 107 whose grip handle 109 extends an adjustable distance beyond handle attachment 85 on the same side of transducer unit 1. Grip frame attachment 107 comprises attachment frame 113 that is fastened about transducer unit 1 in order to provide greater rigidity in use. Grip frame attachment 107 also includes adjustment mechanisms 111 serving to adjustably join grip handle 109 to attachment frame 113 and facilitate the adjustment of the distance that grip handle 109 extends beyond handle attachment 85. Finger handle arrangement 105 is illustrated in an example of use in FIG. 23 wherein grip handle 109 of grip frame attachment 107 is grasped by one hand while individual fingers are extended to push on handle 87 of handle attachment 85. Testing and exercising of finger extensor muscles in groups of fingers and individually is thusly facilitated. Finger handle arrangement 105 is illustrated in a further example of use in FIG. 24 wherein grip handle 109 of grip frame attachment 107 and handle 87 of handle attachment 85 are grasped together between fingers and heel of one hand. Testing and exercising of finger flexor muscles either as a group or by individual fingers is thusly facilitated. Appropriate resilient padding on the handles may be provided to suit particular uses.

Figure 25:
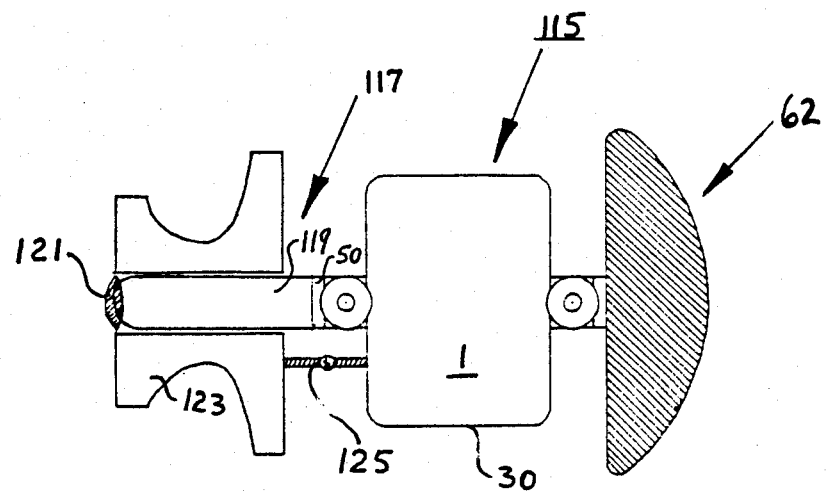
FIG. 25 is a top view of the transducer unit equipped with a mushroom handle attachment and a soft tissue probe attachment incorporating a supplementary sensor as well as a displacement transducer.
Figure 26:
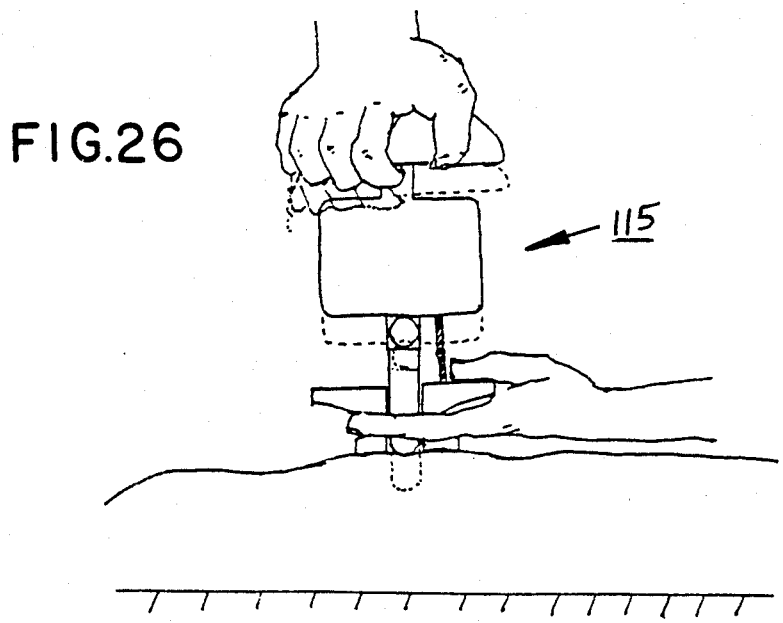
FIG. 26 shows a pictorial illustration of an example of the arrangement of FIG. 25 in a particular use situation.

FIG. 25 depicts a soft tissue probe arrangement 115 for which transducer unit 1 is equipped with mushroom handle attachment 62 at the side of the transducer at which the coupling fastens to the unit housing 30. At the other side there is special tissue probe attachment 117. Tissue probe attachment 117 comprises probe 119 having at one end a standardized male coupler 50, via which the probe is coupled to transducer unit 1. An auxiliary sensor 121 is located and affixed at the free tip of probe 119. Tissue probe attachment 117 further includes sleeve 123 which is axially slidably mounted on probe 119 and is in separate connection with transducer housing 30 via displacement sensor 125. Probe arrangement 115 is further illustrated in an example of use in FIG. 26 wherein it is shown appropriately held with one hand at mushroom handle attachment 62 so as to force the tip of probe 119 of the probe arrangement against particular bodily tissue. The other hand of the user guides sleeve 123 and therewith the entire arrangement during operation. As force is applied against tissue, and probe 119 deflects such tissue in the region of its tip, flange 123 rests on substantially undeflected tissue, thusly facilitating sensing of tissue displacement by displacement sensor 125, whilst deflection force or tissue displacement resistance or strength is sensed by transducer unit 1. In addition, auxiliary sensor 121, which may, for example, comprise an electromyographic sensor and/or a temperature sensor, or other sensor types, may be utilized to provide further simultaneous physiological information. It will be appreciated that appropriate electrical connections are made from auxiliary sensor 121 and displacement sensor 125 either via transducer unit 1 or directly to control processor unit 11 (indicated in FIG. 1). As indicated by example in the illustration of FIG. 26, the shown arrangement may be used to assess, for instance, mhuscle tone in the lumbar paraspinal region. Other physiological measurements useful for medical diagnostic purposes, in therapy and training, may also be obtained by the soft tissue probe arrangement 115.

Figure 27:
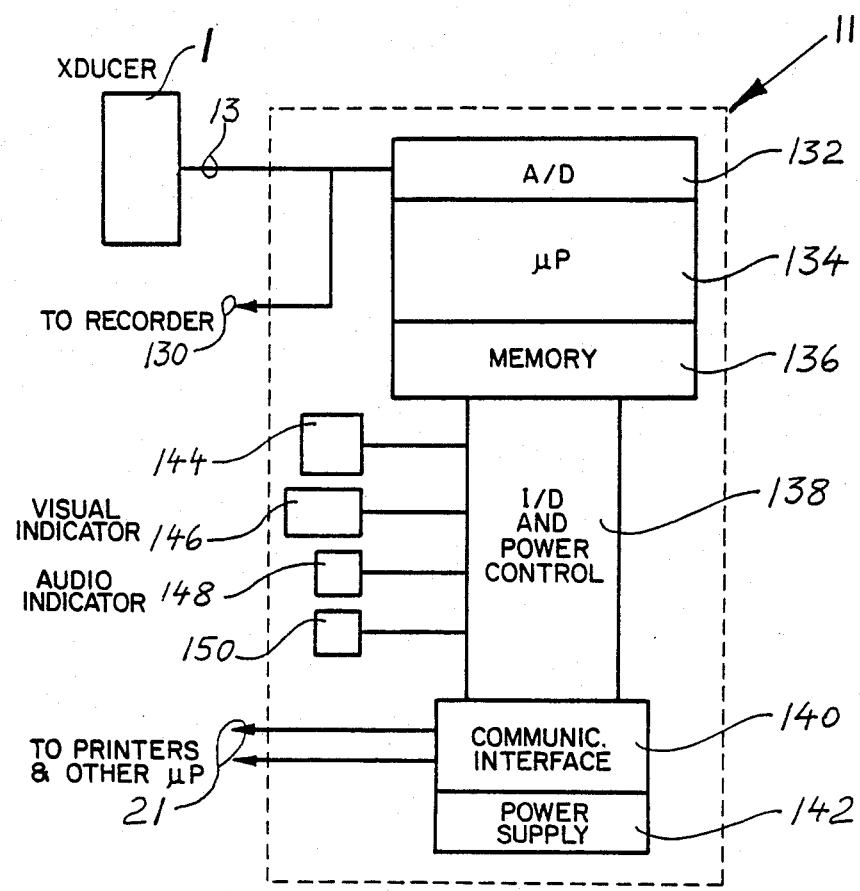
FIG. 27 depicts a schematic block diagram that represents main processing, control and input/output function units of the present invention.

In order to facilitate understanding of system aspects of the present invention, main electronic function units are schematically represented in the block diagram in FIG. 27. The system comprises transducer unit 1 interconnected via umbilical cable 13 with control processor unit 11. Additional auxiliary sensors, as for instance described in conjunction with FIGS. 25 and 26, may be appropriately connected to congtrol processor unit 11, either directly or via transducer unit 1 and umbilical cable 13. Control processor unit 11 comprises appropriately interconnected subunits, such as a central processor unit 134 incorporating a microprocessor and various required supporting function units, a memory unit 136, an input/output and power control unit 138, an analog-to-digital converter unit 132, and a communication interface unit 140. The latter provides for external communication interfacing with, for example, printers, plotters and similar devices, as well as for communication with other computers. Communication connections 21 for such purposes lead from unit 140 to otherwise not shown external devices. An analog output signal 130, substantially representative of the force transducer output, is provided by control processor unit 11 for use by external devices such as analog chart recorders. Control processor unit 11 further comprises a power supply unit 142 for appropriate conversion and provision of electrical power, either from internal batteries or an external power supply. Additionally, control processor unit 11 comprises keyboard unit 144, visual display unit 146, visual indicator unit 148 and audio indicator unit 150, all of which are interconnected with input/output and poswer control unit 138. Analog signals received from transducer unit 1 viaa umbilical cable 13 are first converted to digital form in analog-to-digital converter unit 132 before being passed on to other units for further processing. Central processor unit 134 may comprise also a calendar clock for handling of time-dependent tasks. Visual indicators in unit 148 and/or aaudible indicators of unit 150 may be utilized to provide various forms of biofeedback for muscle training and exercising. It will be appreciated that details of components, interconnections and functional interrelationships of the various units in control processor unit 11 are in accordance with conventional practice appropriately adapted to particular demands of the present system.

The force transducer incorporated in transducer unit 1 may be, for example, a strain gage load cell sold by the Revere Corporation as Model FT70, having a rated force range of 2.2 to 500 pounds. However, other appropriate force sensors with higher or lower force rating levels may also be used.

The apparatus of the present invention is also unique in that its versatility (i.e., ability to test/exercise a wide range of muscle groups) is achieved with a small, lightweight device. Typically, the transducer unit with its permanent couplers weighs about one pound (but no more than five pounds) and is about two inches by one and one-half inches by two and one-half inches, for a volume of seven and one-half cubic inches (but no more than twenty five cubic inches).

While the invention has been particularly shown and described with reference to preferred embodiments thereof, it will be understood by those skilled in the art that various changes and modifications in form and details may be made therein without departing from the spirit and scope of the invention.

What I claim is:

1. Apparatus for testing and exercising a plurality of individual muscle groups of a human subject, said apparatus comprising:
   a housing;
   first and second coupling means extending from within said housing in substantially opposite first and second directions;
   force transducer means disposed within said housing and responsive to forces applied to said first and second coupling means in said first and second directions for providing an electrical force signal representative of the magnitudes of the applied forces;
   at least first and second differently configured engagement means, alternatively connectable to said first coupling means, for applying a first force in at least one of said first and second directions to said force transducer means via said first coupling means, the different configurations of said first and second engagement means being such that said first engagement means is selectively engageable by the human subject in a first manner and that said second engagement means is selectively engageable by the human subject in a second manner which is different from said first manner; and
   at least third engagement means individually and selectively connectable to said second coupling means for applying a second force opposing said first force to said force transducer means via said second coupling means;
   wherein said housing, including said force transducer means and first and second coupling means, weighs no more than five pounds and occupies a volume no greater than twenty five cubic inches.

2. The apparatus according to claim 1 wherein said third engagement means is configured to be selectively engageable by an inanimate force-resisting object to permit said first force to be applied by said human subject at said first coupling means and opposed by said second force applied by said inanimate force-resisting object at said second coupling means.

3. The apparatus according to claim 1 wherein said third engagement means is configured to be selectively engageable by said human subject in a third manner to permit said first and second forces to be applied by two different body segments, respectively, of said human subject.

4. The apparatus according to claim 3 further comprising fourth engagement means having a different configuration from said third engagement means, which, alternatively with said third engagement means, is connectable to said second coupling means for applying said second force to said force transducer means via said second coupling means, said fourth engagement means being configured to be selectively engageable by an inanimate force-resisting object to permit said first force to be applied by said human subject at said first coupling means and opposed said second force applied by said inanimate force resisting object at said second coupling means.

5. The apparatus according to claim 4 wherein said second coupling means include eyelet means, and wherein said fourth engagement means includes hook connector means adapted to engage said eyelet means.

6. The apparatus according to claim 1 wherein said first engagement means includes a convex end adapted to engage an open human palm, and wherein said second engagement means terminates in a strap adapted to be disposed about a human limb.

7. The apparatus according to claim 1 wherein said first engagement means includes a convex end adapted to engage an open human palm, and werein said second engagement means is a handle adapted to be surrounded and gripped by a closed human hand.

8. The apparatus according to claim 1 wherein said first engagement means terminates in a strap adapted to be disposed about a human limb, and wherein said second engagement means is a handle adapted to be surrounded and gripped by a closed human hand.

9. The apparatus according to claim 1 wherein said first and second coupling means are positioned in axial alignment on opposite sides of said transducer means such that forces applied axially to said first and second coupling means are mutually coaxial.

10. The apparatus according to claim 1 wherein said first engagement means comprises:
   a first handle section fixedly secured to said force transducer means;
   a second handle section secured to said first coupling means and disposed between said first handle section and said first coupling means in spaced relation to said first handle section to permit the human subject to alternatively grasp the first engagement means in two alternative positions, namely: a first position in which the first handle section is encircled by a closed palm and fingers of one hand such that the fingers of said one hand are disposed in the space between the first and second handle sections; and a second position in which the fingers of said one hand engage the second handle section and the palm of said one hand engages said first handle section;
   whereby, in said first position the human subject can exert a force on said force transducer means by opening individual fingers of said one hand to urge said first and second handle sections apart such that said second handle section is forced toward said force transducer means; and
   whereby, in said second position the human subject can exert a force on said force transducer means by closing the fingers and palm of said one hand about said first and second handle sections to urge said first and second handle sections toward one another such that said second handle section is forced away from said force transducer means.

11. The apparatus according to claim 1 wherein said third engagement means is a tissue probe arrangement comprising:
   an elongated probe member selectively connectable to said second coupling means and having a distal end;
   a sleeve member disposed surrounding said elongated probe member and having a distal flange portion in a plane located substantially proximate the distal end of said elongated probe member in the absence of any forces applied to said elongated probe and sleeve members; and
   attachment means resiliently securing said sleeve member to said force transducer means to permit longitudinal movement of said elongated probe member relative to said sleeve member when the force transducer means and elongated probe member are forced axially against human tissue at a test location while the distal flange portion of said sleeve member abuts and is restrained by tissue surrounding the test location;
   wherein said force transducer means provides a measurement of tissue strength in the form of said electrical force signal.

12. The apparatus according to claim 11 wherein said attachment means comprises sensor means for providing an indication of the relative displacement between said sleeve and probe members.

13. The apparatus according to claim 11 further comprising a sensor means disposed at said distal end of said probe member for monitoring physiological parameters of said human subject at said test location.

14. The apparatus according to claim 1 further comprising means responsive to said electrical force signal for providing biofeedback indications to said human subject.

15. The apparatus according to claim 1 wherein said force transducer means is responsive to forces in excess of three hundred pounds applied to said actuator means for providing said electrical force signal.

16. The apparatus according to claim 1 wherein said first and second coupling means extend in coaxial alignment from opposite sides of said housing.

17. The apparatus according to claim 1 wherein said first and second coupling means have respective substantially identical coupling members configured to alternatively and interchangeably engage each of said first, second and third engagement means.

18. A testing and exercising apparatus for plural muscles of a human subject comprising:
   force sensing means;
   a plurality of diverse engagement means including first, second and third engagement means;
   first coupling means for mechanically connecting said first and third engagement means alternatively and interchangeably to said force sensing means;
   second coupling means for mechanically connecting said second engagement means to said force sensing means in coaxial alignment with said first coupling means;
   wherein each of said first and second coupling means includes a first and a second coupler, said first and second couplers being mutually attachable;
   wherein said first coupler of said first coupling means and said first coupler of said second coupling means are structurally part of said force sensing means;

wherein said second coupler of said first coupling means is a structural part of said first engagement means, and wherein said second coupler of said second coupling means is a structural part of said second engagement means;

wherein said first and third engagement means are differently configured such that each is adapted to respond to forces exerted by a different muscle, respectively, of said plural muscles; and means for providing an electrical force signal representative of forces applied to said force sensing means via said first and second coupling means.

19. The apparatus according to claim 18 wherein said plurality of diverse engagement means includes:
   at least one handle having a convex end adapted to engage an open human palm;
   at least one strap adapted to be disposed about a human limb; and at least one grip adapted to be surrounded and gripped by a closed human hand.

20. The apparatus according to claim 18 wherein said force sensing transducing unit means, including said first couplers, weighs no more than five pounds and occupies a volume no greater than twenty five cubic inches.

* * * * *